(12) United States Patent
Pujos et al.

(10) Patent No.: US 9,149,659 B2
(45) Date of Patent: Oct. 6, 2015

(54) COSMETIC COMPOSITION FOR INCREASING HYALURONIC ACID SYNTHESIS IN SKIN AND ITS USE FOR REPAIRING WRINKLES

(71) Applicant: Coty Germany GmbH, Mainz (DE)

(72) Inventors: Muriel Pujos, West New York, NJ (US); Dorothee Bernini, Monaco (MC); Cecile Robert, Nice (FR); Olivier Doucet, Roquebrune Cap Martin (FR)

(73) Assignee: Coty Germany GmbH, Mainz (DE)

( * ) Notice: Subject to any disclaimer, the term of this patent is extended or adjusted under 35 U.S.C. 154(b) by 0 days.

(21) Appl. No.: 14/080,171

(22) Filed: Nov. 14, 2013

(65) Prior Publication Data

US 2014/0301960 A1 Oct. 9, 2014

(30) Foreign Application Priority Data

Nov. 14, 2012 (EP) .................................. 12192675

(51) Int. Cl.
| | | |
|---|---|---|
| *A61K 8/97* | (2006.01) | |
| *A61Q 19/08* | (2006.01) | |
| *A61K 38/06* | (2006.01) | |
| *C07K 5/08* | (2006.01) | |
| *A61Q 1/02* | (2006.01) | |
| *A61K 8/64* | (2006.01) | |
| *A61Q 17/04* | (2006.01) | |
| *A61Q 19/00* | (2006.01) | |
| *A61Q 19/04* | (2006.01) | |

(52) U.S. Cl.
CPC ... *A61Q 1/02* (2013.01); *A61K 8/64* (2013.01); *A61K 8/97* (2013.01); *A61Q 17/04* (2013.01); *A61Q 19/007* (2013.01); *A61Q 19/04* (2013.01); *A61Q 19/08* (2013.01)

(58) Field of Classification Search
CPC ........... A61K 8/64; A61K 8/97; A61Q 19/08; A61Q 19/04; A61Q 17/04; A61Q 19/007; A61Q 1/02

See application file for complete search history.

(56) References Cited

U.S. PATENT DOCUMENTS

2010/0247563 A1  9/2010 Hines et al.

FOREIGN PATENT DOCUMENTS

| FR | 2759910 A1 * | 8/1998 | ............ A61K 35/78 |
|---|---|---|---|
| WO | 2010082175 | 7/2010 | |
| WO | 2011110793 | 9/2011 | |

OTHER PUBLICATIONS

Machine translation of FR 2759910 A1, pp. 1-6, accessed Nov. 3, 2014.*
Tallarida, Drug synergism and dose-effect data analysis, CRC Press LLC, 2000, pp. 1-29.*
"Facial serum", Mintel (2011). (4 pages).
"Matrixyl synthe' 6", (Jan. 1, 2010). Retrieved on Mar. 26, 2013 from http://vellura.com/Matrixyl-synthe'6%20(1).pdf.

* cited by examiner

*Primary Examiner* — Julie Ha
*Assistant Examiner* — Li Ni Komatsu
(74) *Attorney, Agent, or Firm* — Novak Druce Connolly Bove + Quigg LLP

(57) ABSTRACT

The present invention relates to a skin composition which has an excellent effect on smoothing or repairing wrinkles. The composition comprises Palmitoyl Tripeptide-38 (Palmitoyl-Lysyl-Dioxymethionyl-Lysine) and *Piper nigrum* (Pepper) seed Extract which combination has been found to result in a synergistic effect on hyaluronan synthase 1 (HAS1) mRNA expression in human fibroblasts. The hyaluronan synthase is responsible for the synthesis of hyaluronan (hyaluronic acid) in skin. Hyaluronic acid is a constituent of the extracellular matrix of the skin and responsible for space filling, tissue repair and retention of moisture.

17 Claims, 2 Drawing Sheets

COSMETIC COMPOSITION FOR INCREASING HYALURONIC ACID SYNTHESIS IN SKIN AND ITS USE FOR REPAIRING WRINKLES

This Application claims priority to European patent application No. 12192675.2, filed Nov. 14, 2012, entitled "Cosmetic composition for increasing hyaluronic acid synthesis in skin and its use for repairing wrinkles", the entirety of which is incorporated herein by reference.

The present invention relates to a skin composition which has an excellent effect on smoothing or repairing wrinkles. The composition comprises Palmitoyl Tripeptide-38 (Palmitoyl-Lysyl-Dioxymethionyl-Lysine) and *Piper nigrum* (Pepper) seed Extract which combination has been found to result in a synergistic effect on hyaluronan synthase 1 (HAS1) mRNA expression in human fibroblasts. The hyaluronan synthase is responsible for the synthesis of hyaluronan (hyaluronic acid) in skin. Hyaluronic acid is a constituent of the extracellular matrix of the skin and responsible for space filling, tissue repair and retention of moisture.

It was the problem of the present invention to provide an anti wrinkle composition with superior wrinkles repairing effect.

It was found by the inventors of the present application that this problem can be solved with a cosmetic composition which comprises as active substances
0.000025 to 0.001 wt % Palmitoyl-Lysyl-Dioxymethionyl-Lysine,
0.00105 to 0.063 wt % *Piper nigrum* (pepper) seed extract, water and cosmetically acceptable auxiliaries, wherein the given percentages relate to the total weight of the composition.

Figure 1:
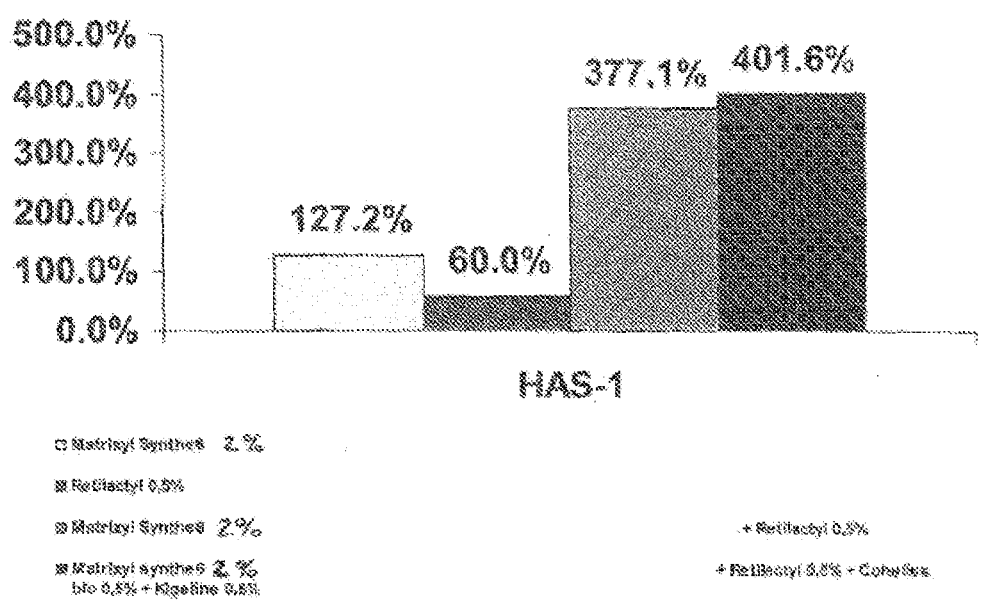
FIG. 1 is a chart showing the percentage of HAS-1 mRNA expression in normal human fibroblasts for various compositions.

It is known in the art that Palmitoyl-Lysyl-Dioxymethionyl-Lysine which INCI name is Palmitoyl Tripeptide-38 stimulates the synthesis of skin matrix molecules such as dermis collagen and epidermal hyaluronic acid and helps fill wrinkles. A commercially available product which comprises this tripeptide is Matrixyl®Synthe'6™ (Sederma, France). The INCI name of Matrixyl®Synthe'6™ is Glycerin (and) Water (and) Hydroxypropyl Cyclodextrin (and) Palmitoyl Tripeptide-38. The product comprises 0.025 wt % Palmitoyl Tripeptide-38, 78.975 wt % glycerin, 1.0 wt % hydroxypropyl cyclodextrin and the remainder to 100 wt % water.

In a further embodiment of the invention the cosmetic composition comprises 0.000125 to 0.00075 wt % Palmitoyl Tripeptide-38 related to the total weight of the composition, preferably 0.00025 to 0.00075 wt %.

*Piper nigrum* (Pepper) seed Extract is described in the art to be obtained from black pepper berries by powdering them and subjecting the aqueous solution of the powder to enzymatic hydrolysis. It is rich in polysaccharides, glucans and rhamnogalacturonans. A commercially available product which comprises this *piper nigrum* (Pepper) seed Extract is Retilactyl D® (Silab, France). This product comprises 2.1 wt % *piper nigrum* seed extract, stabilizer, preservative and 97.2 wt % water (INCI: Water (and) *Piper nigrum* (Pepper) seed extract). Retilactyl D® was designed to help to mitigate the affects of photoageing on reticular fibroblasts.

In a further embodiment of the invention the cosmetic composition comprises 0.0021 to 0.0315 wt % *Piper nigrum* (Pepper) seed extract related to the total weight of the composition, preferably 0.0042 to 0.021 wt %.

Surpassingly, it has now been found that the combination of Palmitoyl Tripeptide-38 and *Piper nigrum* (Pepper) seed extract has a synergistic effect on synthesis of HAS1 mRNA in normal human fibroblasts. This way the level of dermis hyaluronic acid in the skin is effectively increased. Using e.g. 2 wt % Matrixyl®Synthe'6™ (which corresponds to 0.0005 wt % Palmitoyl Tripeptide-38) and 0.5 wt % Retilactyl D® (which corresponds to 0.0105 wt % *Piper nigrum* seed extract) the HAS1 mRNA expression increased to 377%, whereas the HAS1 mRNA expression of Matrixyl®Synthe'6™ alone was 127% and that of Retilactyl D® alone was 60% (compare example 4 and FIG. 1).

It has revealed that the anti wrinkle composition of the present invention can be further improved by adding *Secale cereale* (rye) seed extract and/or *Kigelia africana* fruit extract. By adding both actives the HAS1 mRNA expression could be further improved to 401% (compare FIG. 1).

*Secale cereale* (rye) seed extract is described in the art to be obtained by subjecting the aqueous solution of rye flakes to enzymatic hydrolysis. A commercially available product which comprises this rye seed extract is Coheliss®Bio (Silab, France). The product comprises 6 wt % rye seed extract, 93.7 wt % water and 0.3 wt % preservative (INCI: Water & *Secale cereale* (rye) seed extract). The cosmetic composition of the invention comprises 0.003 to 0.18 wt % *Secale cereale* (rye) seed extract, related to the total weight of the composition, preferably 0.006 to 0.09 wt %, more preferred 0.006 to 0.06 wt %.

*Kigelia africana* fruit extract is obtained from the fruits of the *Kigelia africana* tree by hydroglycolic extraction. A commercially available product which comprises this extract is Kigeline (Greentech, France). The product comprises about 1.08 wt % *Kigelia africana* fruit extract, 39.0 to 39.9 wt % butylene glycol and the remainder to 100 wt % water (INCI: Water, Butylene Glycol, *Kigelia africana* fruit extract). The cosmetic composition of the invention comprises 0.000054 to 0.0324 wt % *Kigelia africana* fruit extract related to the total weight of the composition, preferably 0.00108 to 0.0162 wt %, more preferred 0.00108 to 0.0108 wt %.

The composition of the invention comprises auxiliary substances which are selected from the group comprising one or more of emulsifiers, emollients, humectants, moisturizers, antioxidants, gelling agents, chelating or complexing agents, viscosity modulating agents, opacifiers, preservatives, colorants, fragrances, skin care agents, tanning agents, UV filters, buffers, solvents, and mixtures thereof.

The cosmetic composition of the invention is formulated as O/W or W/O emulsion. The emulsifiers which can be used for this purpose are well known by the skilled person. According to the invention examples of emulsifiers which can be used are: Polyacrylamide (and) C13-C14 Isoparaffin (and) Laureth-7 (Trade name: Sepigel 305), PEG-40 Stearate (Myrj S40), Glyceryl Stearate (Trade name: Cutina GMS V), PPG-1-PEG-9 Lauryl Glycol Ether (Trade name: Eumulgin L), PEG-60 Hydrogenated Castor Oil (Trade name: Cremophor CO 60), Cetyl Alcohol and Glyceryl Stearate and PEG-75 Stearate and Ceteth-20 and Steareth-20 (Trade name: Emulium Delta), Cetearyl Alcohol (Trade name: Nafol 1618), Hydroxyethyl Acrylate/Sodium Acryloyldimethyl Taurate Copolymer and water and Squalane and Polysorbate 60 and Sorbitan Isostearate (Trade name: Simulgel NS).

The composition according to the present invention comprises 0.01 to 3.0 wt % antioxidants, preferably 0.05 to 1.0 wt %, more preferred 0.08 to 0.3 wt %, wherein the given percentages relate to the total weight of the composition. Suitable antioxidants are for instance vitamin C and its derivates, e.g. ascorbyl acetate, ascorbyl phosphate, ascorbyl palmitate, vitamin E, derivates of vitamin E, a plant extract mixture comprising *Angelica Archangelica* Root Extract, *Camellia Sinensis* Leaf Extract, *Pongamia Pinnata* Seed Extract and *Coffea Arabica* Seed Extract (RPF complex), and mixtures thereof. For instance Oxynex K (Merck) which is a mixture of tocopherol, ascorbyl palmitate, citric acid, ascorbic acid and PEG can be included into the present composition.

The RPF complex which may be used in the cosmetic composition of the invention includes preferably extracts from green coffee beans, from leaves of green tea (*Camellia sinensis*), from seeds of *Pongamia pinnata*, from roots of *Angelica archangelica* and from peel of *Citrus aurantium* (Bitter orange). The extracts are prepared by extraction with a monovalent or multivalent alcohol or a mixture of such alcohol(s) with water at room temperature (about 15-30° C.). The extracts are used in liquid or dried form. An especially preferred plant extract mixture is a mixture of liposomic encapsulated plant extracts of 1-4% *Camellia Sinensis* Leaf Extract, 1-4% Green Coffee Seed Extract, 1-4% *Pongamia Pinnata* Seed Extract, 1-4% *Angelica Archangelica* Root Extract, 1-4% *Citrus Aurantium* Peel Extract, 2-10% phospholipids in an aqueous-alcoholic suspension wherein the alcohol content is in the range of 4-12%, wherein all concentrations are related to the weight of the plant extract mixture.

According to the invention emollients can be added to soften and smoothen the skin. Suitable emollients are for instance Caprylic/Capric Triglyceride, Ethylhexyl Palmitate, silicones, such as dimethicone, Polysilicone-11, siloxanes, such as Cyclopenta-siloxane/Dimethiconol, Cyclohexasiloxane; Butyrospermum Parkii (Shea) Butter. Further suitable emollients are for example Cetearyl Isononanoate, Octyldodecanol, Isopropyl Palmitate, Isopropyl Myristate, Mineral Oils, Isohexadacane, Diisopropyl Sebacate, C12-15 Alkyl Benzoate, Propylheptyl Caprylate, Pentaerythrityl tetraisostearate, Cetearyl Isononanoate, Isononyl Isononanoate, Ethyl Hexyl Hydroxystearate, Phenoxyethyl Caprylate, Isoamyl Cocoate.

In an advantageous embodiment of the invention the composition contains moisturizing substances in a range of 0.1 to 10.0 wt %. Preferred moisturizers which may be used are glycerine, propylene glycol and butylene glycol. Additionally, hyaluronic acid microspheres (Trade name: Filling Spheres™ hyaluronic, BASF) may be added from 0.01 to 2 wt %, related to the total weight of the composition, preferably 0.01 to 0.2 wt %, wherein the microspheres contain 0.2 wt % sodium hyaluronate.

The composition of the present invention has an excellent wrinkle correcting effect, mainly based on increased dermis hyaluronic acid synthesis in skin. Therefore, it is another object of the present application to provide a composition for use in increasing hyaluronic acid synthesis in skin and to provide a composition for use in repairing or smoothing wrinkles, preferably facial wrinkles. Yet another object of the present invention is a method for treating wrinkles on skin, preferably facial wrinkles, by applying the composition of the present invention to skin areas with wrinkles to be treated.

The compositions of the present invention are prepared in a manner well known for O/W or W/O emulsions in cosmetic industries. Details of the preparation are given in the examples.

The following examples are offered to illustrate the cosmetic compositions of the present invention and their preparation. They are not intended to be limiting in any respect.

EXAMPLE 1

| | DAY CREAM | | | |
|---|---|---|---|---|
| | INCI Name/description of ingredients | A % | B % | B % |
| Phase 1 | WATER | q.s. | q.s. | q.s. |
| | COLORANT ACID RED 27 | 0.00015 | 0.00025 | 0.0005 |
| | STYRENE/ACRYLATES COPOLYMER (hydro) | 0.8 | 1.40 | 1.80 |
| | GLYCERIN | 2.0 | 4.0 | 6.0 |
| | POLYACRYLAMIDE, WATER, C13-14 ISOPARAFFIN, LAURETH 7 | 4.9 | 4.7 | 4.5 |
| Phase 2 | HYDROGENATED POLYISOBUTENE | 4.0 | 2.7 | 1.5 |
| | CYCLOPENTASILOXANE & DIMETHICONOL | 2.0 | 2.8 | 3.5 |
| Phase 3 | *SECALE CEREALE* (RYE) SEED EXTRACT (hydro) (Coheliss ®Bio) | 0.1 | 2.0 | 0.6 |
| | *KIGELIA AFRICANA* FRUIT EXTRACT (hydroglycolic) (Kigeline) | 0.15 | 2.5 | 0.6 |
| | MICROSPHERES SODIUM HYALURONATE (Hyaluronic filling spheres) | 0.05 | 0.12 | 0.08 |
| | ENCAPSULATED INGREDIENTS RPF COMPLEX | 0.35 | 0.25 | 0.15 |
| | HYDROLYZED *CITRUS AURANTIUM DULCIS* FRUIT EXTRACT (hydro) | 1.5 | 1.0 | 0.7 |
| | *MAURITIA FLEXUOSA* FRUIT OIL | 0.5 | 0.4 | 0.3 |
| | BIFIDA FERMENT LYSATE | 0.1 | 2.0 | 0.6 |
| | GLYCERIN & WATER & HYDROXYPROPYL CYCLODEXTRIN & PALMITOYL TRIPEPTIDE-38 (Matrixyl ®Synthe`6 ™) | 0.3 | 3.5 | 2.0 |
| | PIPER NIGRUM (PEPPER) SEED EXTRACT (hydro) (Retilactyl D ®) | 0.25 | 2.0 | 0.45 |
| Phase 4 | NYLON-12 | 1.0 | 1.9 | 1.7 |
| | PTFE | 1.5 | 1.2 | 1.5 |

-continued

DAY CREAM

| | INCI Name/description of ingredients | A % | B % | B % |
|---|---|---|---|---|
| Phase 5 | FRAGRANCE | 0.1 | 0.25 | 0.4 |
| | PHENOXYETHANOL | 0.5 | 0.5 | 0.5 |
| | 1,2-HEXANEDIOL, CAPRYLYL GLYCOL | 0.5 | 0.5 | 0.5 |
| | | 100 | 100 | 100 |

Preparation:

Add separately all ingredients of phase 1 to the water with stirring at room temperature.

Mix well to obtain a homogenous phase.

Add the ingredients of phase 2 to phase 1, homogeneize well under stirring.

Add separately and slowly all the ingredients of phase 3 to phase 1, 2.

Stir well till homogenously.

Continue in the same way adding phase 4 and 5 to phase 1, 2, 3.

Control homogeneity of the final product.

EXAMPLE 2

| | | EYE CREAM | | |
|---|---|---|---|---|
| | INCI Name/description of ingredients | A example 1 % | B example 2 % | C example 3 % |
| Premix | GLYCERIN | 2.0 | 4.0 | 6.0 |
| | XANTHAN GUM | 0.1 | 0.15 | 0.2 |
| Phase 1 | WATER | q.s. | q.s. | q.s. |
| | COLORANT ACID RED 27 | 0.0005 | 0.0007 | 0.0009 |
| | FD & C YELLOW N°5 | 0.0005 | 0.001 | 0.0015 |
| | DISODIUM EDTA | 0.035 | 0.040 | 0.0450 |
| | CAFFEINE | 0.3 | 0.2 | 0.25 |
| | PROPYLENE GLYCOL | 1.5 | 1.5 | 2.3 |
| | CARBOMER | 0.2 | 0.15 | 0.1 |
| Phase 2 | GLYCERYL STEARATE | 4.0 | 3.8 | 3.3 |
| | PEG-40 STEARATE | 1.2 | 1.5 | 1.7 |
| | SYNTHETIC BEESWAX | 2.5 | 2.7 | 3.3 |
| | HYDROGENATED POLYISOBUTENE | 1.0 | 2.0 | 2.7 |
| | *BUTYROSPERMUM PARKII* (SHEA) BUTTER | 3.5 | 3.0 | 3.5 |
| | STEARYL ALCOHOL & CETEARETH-20 | 4.3 | 4.6 | 4.8 |
| Phase 3 | CYCLOPENTASILOXANE & DIMETHICONOL | 1.5 | 3.5 | 2.5 |
| | CYCLOPENTASILOXANE & CYCLOHEXASILOXANE | 2.5 | 1.5 | 2.5 |
| Phase 4 | KAOLIN | 0.7 | 1.0 | 1.5 |
| | NYLON-12 | 2.0 | 1.5 | 1.0 |
| | MICA & SILICA & TITANIUM DIOXIDE | 0.3 | 0.4 | 0.45 |
| Phase 5 | SODIUM HYDROXIDE (hydro) | q.s. | q.s. | q.s. |
| Phase 6 | *KIGELIA AFRICANA* FRUIT EXTRACT (hydroglycolic) (Kigeline) | 0.1 | 2.0 | 0.6 |
| | *GINGKO BILOBA* LEAF EXTRACT (hydroglycolic) | 0.6 | 0.6 | 0.6 |
| | *AESCULUS HIPPOCASTANUM* (HORSE CHESTNUT) SEED EXTRACT (hydroglycerin) | 0.4 | 0.4 | 0.4 |
| | *SECALE CEREALE* (RYE) SEED EXTRACT (hydro) (Coheliss ®Bio) | 0.2 | 1.9 | 0.4 |
| | MICROSPHERES SODIUM HYALURONATE (Hyaluronic filling spheres) | 0.05 | 0.12 | 0.08 |
| | ENCAPSULATED INGREDIENTS RPF COMPLEX | 0.25 | 0.2 | 0.15 |
| | PEG-6 ISOSTEARATE & HESPERETIN LAURATE | 0.2 | 0.2 | 0.2 |
| | BIFIDA FERMENT LYSATE | 0.2 | 3.0 | 0.6 |
| | | 3.0 | 0.2 | 2.0 |
| | GLYCERINS WATER & HYDROXYPROPYL CYCLODEXTRIN & PALMITOYL TRIPEPTIDE-38 (Matrixyl ®Synthe´6 ™) | | | |
| | | 0.25 | 2.0 | 0.45 |
| | *PIPER NIGRUM* (PEPPER) SEED EXTRACT (hydro) (Retilactyl D ®) | | | |

-continued

| | EYE CREAM | | | |
|---|---|---|---|---|
| | INCI Name/description of ingredients | A example 1 % | B example 2 % | C example 3 % |
| Phase 7 | FRAGRANCE | 0.05 | 0.1 | 0.15 |
| | PHENOXYETHANOL, | 0.5 | 0.5 | 0.5 |
| | 1,2-HEXANEDIOL, CAPRYLYL GLYCOL | 0.5 | 0.5 | 0.5 |
| | TOTAL | 100 | 100 | 100 |

Preparation:

Dissolve the ingredients of phase 1 in the water and heat up to approximately 75° C.

Heat separately phase 2 to approximately 75° C.

Prepare premix till homogeneity and add it to phase 1 stir well.

Put phase 2 in phase 1 under stirring and homogeneizing.

Cool down the homogenous emulsion phase 1, 2 to 50-55° C.

Add phase 3 and 4 separately to phase 1, 2; continue stirring.

Neutralisation of phase 1, 2, 3, 4 with phase 5 under stirring.

Homogeneize well.

Cool with gentle stirring below 40° C. and continue the adding of all ingredients from phase 6 to phase 1, 2, 3, 4, 5, control homogeneity.

Cool again with gentle stirring till 20-25° C., add the ingredients of phase 7 to phase 1, 2, 3, 4, 5, 6.

Control final homogeneity.

EXAMPLE 3

| | NIGHT CREAM | | | |
|---|---|---|---|---|
| | INCI Name/description of ingredients | A example 1 % | B example 2 % | C example 3 % |
| Premix | GLYCERIN | 3.0 | 3.5 | 4.0 |
| | XANTHAN GUM | 0.6 | 0.5 | 0.65 |
| Phase 1 | WATER | q.s. | q.s. | q.s. |
| | COLORANT ACID RED 27 | 0.0001 | 0.0002 | 0.0003 |
| | BUTYLENE GLYCOL | 2.0 | 1.5 | 2.5 |
| Phase 2 | CAPRYLIC/CAPRIC TRIGLYCERIDE | 3.0 | 2.0 | 3.5 |
| | GLYCERYL STEARATE | 2.5 | 2.2 | 1.85 |
| | CETYL ALCOHOL | 4.0 | 3.5 | 4.3 |
| | ETHYLHEXYL PALMITATE | 3.0 | 4.0 | 2.5 |
| | *BUTYROSPERMUM PARKII* (SHEA) BUTTER | 3.0 | 3.5 | 4.5 |
| | SORBITAN TRISTEARATE | 0.2 | 0.2 | 0.2 |
| Phase 3 | CYCLOPENTASILOXANE & DIMETHICONOL | 5.0 | 2.0 | 4.0 |
| Phase 4 | METHYL METHACRYLATE CROSSPOLYMER | 1.7 | 3.0 | 2.5 |
| | NYLON-12 | 1.0 | 1.5 | 2.0 |
| Phase 5 | *KIGELIA AFRICANA* FRUIT EXTRACT (hydroglycolic) (Kigeline) | 0.2 | 3.0 | 0.6 |
| | HYDROLYZED *CITRUS AURANTIUM DULCIS* FRUIT EXTRACT (hydro) | 2.0 | 1.2 | 0.6 |
| | *MAURITIA FLEXUOSA* FRUIT OIL | 0.2 | 0.25 | 0.3 |
| | *SECALE CEREALE* (RYE) SEED EXTRACT (hydro) (Coheliss ®Bio) | 0.25 | 2.3 | 0.6 |
| | ENCAPSULATED INGREDIENTS RPF COMPLEX | 0.25 | 0.2 | 0.15 |
| | DECARBOXY CARNOSINE HCL (hydroglycolic) | 0.25 | 0.1 | 0.15 |
| | BIFIDA FERMENT LYSATE | 0.3 | 3.5 | 0.55 |
| | GLYCERINS WATER & HYDROXYPROPYL CYCLODEXTRIN & PALMITOYL TRIPEPTIDE-38 (Matrixyl ®Synthe´ 6 ™) | 0.5 | 3.5 | 2.0 |
| | *PIPER NIGRUM* (PEPPER) SEED EXTRACT (hydro) (Retilactyl D ®) | 0.3 | 2.5 | 0.45 |
| Phase 6 | FRAGRANCE | 0.1 | 0.2 | 0.3 |
| | PHENOXYETHANOL | 0.5 | 0.5 | 0.5 |
| | 1,2-HEXANEDIOL, CAPRYLYL GLYCOL | 0.5 | 0.5 | 0.5 |
| | HYDROXYETHYL ACRYLATE & SODIUM ACRYLOYLDIMETHYL | | | |

-continued

NIGHT CREAM

| INCI Name/description of ingredients | A example 1 % | B example 2 % | C example 3 % |
|---|---|---|---|
| TAURATE COPOLYMER & SQUALANE & POLYSORBATE 60 | 3.5 | 3.9 | 3.7 |
| TOTAL | 100 | 100 | 100 |

Preparation:

Dissolve the ingredients of phase 1 in the water and heat up to approximately 75° C.

Heat separately phase 2 to approximately 75° C.

Prepare premix till homogeneity and add it to phase 1 stir well.

Put phase 2 in phase 1 under stirring and homogeneizing.

Cool down the homogenous emulsion phase 1, 2 to 50-55° C. with stirring.

Add phases 3 and 4 separately to phase 1, 2; continue stirring.

Homogeneize well.

Cool with gentle stirring phase 1, 2, 3, 4 below 35° C. and continue the adding of all ingredients from phase 5 to phase 1, 2, 3, 4, control homoneneity.

Cool again with gentle stirring till 20-25° C., add the fragrance, the preservatives and the blend of gel to the phase 1, 2, 3, 4, 5.

Control final homogeneity.

EXAMPLE 4

Test Protocol of HAS1 mRNA Expression Measurement

Normal human fibroblasts were treated by the active ingredient/mixture of active ingredients diluted in the cell culture medium for 3 hours at 37° C., 5% $CO_2$. Non treated cells were incubated in the same conditions with cell culture medium.

The HAS1 mRNA expression was then assessed by using the Real-Time (RT) PCR (reverse transcription polymerase chain reaction) technology. For that purpose, total RNA were extracted with the ABI Prism 6100 Nucleic acid prepstation (Applied Biosystems) and quantified with a spectrophotometer at 260 nm. First strand cDNA synthesis was performed using 2 µg of total RNA with the High Capacity cDNA Archive kit. Real-Time PCR was carried out on 10 ng of cDNA with the 7300 Real Time PCR System by using the TaqMan primers and probe (Applied Biosystems) specific to HAS1. Amplification conditions were as follows: 15 sec at 95° C., 1 min at 60° C. for 40 cycles. Relative changes in gene expression were calculated according to the $2^{-\Delta\Delta CT}$ method with the 7300 System Software™.

The results are demonstrated in following table 1 and in FIG. 1. FIG. 1 shows the HAS1 mRNA expression measured with RT-PCR on normal human fibroblasts.

TABLE 1

| | HAS1 mRNA expression | | | |
|---|---|---|---|---|
| | Treatment 3 h | | Treatment 6 h | |
| | Stimulation (%) (/Untreated) | Statistical analysis | Stimulation (%) (/Untreated) | Statistical analysis |
| | Synergy with 2 ingredients: | | | |
| Matrixyl 2% | 127.2% | s/untreated | 59.6% | s/untreated |
| Retilactyl 0.5% | 60.0% | s/untreated | 78.9% | s/untreated |
| Mix: Matrixyl 2% + Retilactyl 0.5% | 377.1% | s/untreated s/each ingredient | 289.4% | s/untreated s/each ingredient | s/untreated: statistically significant compared to untreated cells
s/each ingredient: Mix statistically significant compared to each ingredient As it can be taken from the results, the combination of 2% Matrixyl Synthe'™ (which corresponds to 0.0005 wt % Palmitoyl Tripeptide-38) and 0.5% Retilactyl D® (which corresponds to 0.0105 wt % *Piper nigrum* seed extract) increased the HAS1 mRNA expression to 377.1%, whereas the HAS1 mRNA expression of Matrixyl®Synthe'6™ alone was 127.2% and that of Retilactyl D® alone was 60%. Addition of 0.5% Coheliss®Bio (which corresponds to 0.03 wt % *Secale cereale* (rye) seed extract) and 0.5% Kigeline (which corresponds to 0.0054 wt % *Kigelia africana* fruit extract) further improved the HAS1 mRNA expression to 401.6%.

EXAMPLE 5

Exploration of the Activity of a Finished Product of the Invention on Hyaluronan on Living Human Skin Explant The day cream C of Example 1 with 2% Matrixyl and 0.5% of each of Retilactyl, Coheliss Bio and Kigeline was tested with regard to its activity on dermis hyaluronic acid synthesis.

The explants were kept in survival in BEM culture medium at 37° C. in a humid, 5% $CO_2$ atmosphere. The product tested was applied on days D0, D2 and D4 on the basis of 2 mg/cm². Half of the culture medium was renewed on D2 and D4. The control explant did not receive any treatment.

On D0, 3 explants were collected and cut in two parts. One half was fixed in buffered formalin, and the other half was frozen at −80° C. On D5, 3 explants treated or not with the product were collected and processed in the same way.

The frozen sample were cut into 7 µm thick sections using a Leica CM 3050 cryostat. Immunostaining of HA was realized on frozen sections with a biotinylated HABP (Seikagaku ref 400763-1A) for 1 hour at room temperature. The staining was revealed using Streptavidin/FITC (Caltag, SA 1001).

The immunostaining was assessed by microscopical observation using Leica filter block 13 (FITC) for HABP and by image analysis. It revealed that hyaluronic acid synthesis improved of 61%.

Figure 2:
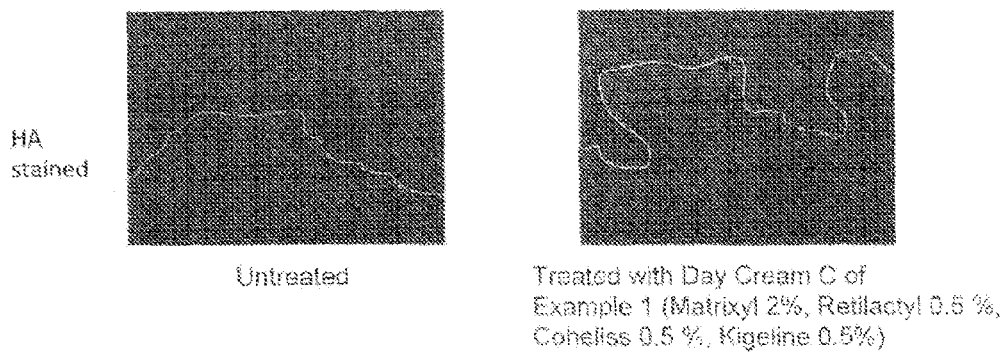
FIG. 2 shows the immunostaining results of this in vitro test on normal human skin. Hyaluronic acid is stained in green.

FIG. 2 shows the immunostaining results of this in vitro test on normal human skin. Hyaluronic acid is stained in green.

The invention claimed is:

1. A cosmetic composition for increasing hyaluronic acid synthesis in skin, the composition comprising:
0.000025 to 0.001 weight percent of Palmitoyl-Lysyl-Dioxymethionyl-Lysine;
0.00105 to 0.063 weight percent of *Piper nigrum* seed extract;
water; and
cosmetically acceptable auxiliaries,
wherein all given percentages relate to a total weight of the composition.

2. The composition according to claim 1, comprising: 0.003 to 0.18 weight percent of *Secale cereale* seed extract, wherein all given percentages relate to the total weight of the composition.

3. The composition according to claim 1, comprising: 0.000054 to 0.0324 weight percent of *Kigelia africana* fruit extract, wherein all given percentages relate to the total weight of the composition.

4. The composition according to claim 1, comprising: 0.000125 to 0.00075 weight percent of Palmitoyl-Lysyl-Dioxymethionyl-Lysine, wherein all given percentages relate to the total weight of the composition.

5. The composition according to claim 1, comprising: 0.0021 to 0.0315 weight percent of *Piper nigrum* seed extract, wherein all given percentages relate to the total weight of the composition.

6. The composition according to claim 1, comprising: 0.006 to 0.09 weight percent of *Secale cereale* seed extract, wherein all given percentages relate to the total weight of the composition.

7. The composition according to claim 1, comprising: 0.00108 to 0.0162 weight percent of *Kigelia africana* fruit extract, wherein all given percentages relate to the total weight of the composition.

8. The composition according to claim 1, comprising: one or more auxiliary substances selected from the group consisting of emulsifiers, emollients, humectants, moisturizers, gelling agents, chelating agents, complexing agents, viscosity modulating agents, opacifiers, preservatives, colorants, fragrances, skin care agents, tanning agents, ultraviolet (UV) filters, buffers, solvents, and mixtures thereof.

9. The composition according to claim 2, comprising: 0.000054 to 0.0324 weight percent of *Kigelia africana* fruit extract, wherein all given percentages relate to the total weight of the composition.

10. The composition according to claim 1, comprising: 0.00025 to 0.00075 weight percent of Palmitoyl-Lysyl-Dioxymethionyl-Lysine, wherein all given percentages relate to the total weight of the composition.

11. The composition according to claim 1, comprising: 0.0042 to 0.021 weight percent of *Piper nigrum* seed extract, wherein all given percentages relate to the total weight of the composition.

12. The composition according to claim 2, comprising: 0.006 to 0.09 weight percent of *Secale cereale* seed extract, wherein all given percentages relate to the total weight of the composition.

13. The composition according to claim 2, comprising: 0.00108 to 0.0162 weight percent of *Kigelia africana* fruit extract, wherein all given percentages relate to the total weight of the composition.

14. A method for treating wrinkles on skin, the method comprising: applying the cosmetic composition according to claim 1 to skin areas with wrinkles to be treated.

15. The method according to claim 14, wherein the wrinkles are facial wrinkles.

16. The method according to claim 14, wherein the cosmetic composition comprises 0.006 to 0.09 weight percent of *Secale cereale* seed extract, and wherein all percentages relate to the total weight of the composition.

17. The method according to claim 14, wherein the cosmetic composition comprises 0.00108 to 0.0162 weight percent of *Kigelia africana* fruit extract, and wherein all given percentages relate to the total weight of the composition.

* * * * *